United States Patent [19]

Jones

[11] Patent Number: 5,739,172
[45] Date of Patent: Apr. 14, 1998

[54] ENVIRONMENTALLY SAFE PESTICIDE COMPOSITIONS

[75] Inventor: Keith A. Jones, Yardley, Pa.

[73] Assignee: Church & Dwight Co., Inc., Princeton, N.J.

[21] Appl. No.: 40,346

[22] Filed: Mar. 30, 1993

Related U.S. Application Data

[62] Division of Ser. No. 907,050, Jul. 1, 1992, Pat. No. 5,342,630.

[51] Int. Cl.$^6$ .............................. A61K 7/075; C11D 9/12
[52] U.S. Cl. ........................... 514/881; 424/717; 510/160
[58] Field of Search ................ 424/70, 717; 514/880, 514/881; 252/DIG. 13; 510/160

[56] References Cited

U.S. PATENT DOCUMENTS

| | | | |
|---|---|---|---|
| 3,805,809 | 4/1974 | Zeffren et al. | 132/203 |
| 4,026,825 | 5/1977 | Steen et al. | 252/547 |
| 4,298,494 | 11/1981 | Parslow et al. | 252/174.16 |
| 4,371,461 | 2/1983 | Jones et al. | 252/547 |
| 4,452,732 | 6/1984 | Bolich, Jr. | 252/547 |
| 4,668,434 | 5/1987 | Bowman | 512/4 |
| 5,047,424 | 9/1991 | Puritch et al. | 514/521 |
| 5,064,859 | 11/1991 | Crammer et al. | 514/560 |
| 5,073,274 | 12/1991 | Caswell | 252/8.6 |

*Primary Examiner*—Robert H. Harrison
*Attorney, Agent, or Firm*—Irving Fishman

[57] ABSTRACT

This invention provides a novel pesticide composition having a bicarbonate-containing inorganic salt ingredient which exhibits fungicidal activity, and which enhances the efficacy of a $C_8$–$C_{22}$ fatty acid insecticidal ingredient for the treatment of agricultural and horticultural plants. An invention pesticide composition also can contain a water-soluble organic compound which functions as a compatibility enhancing agent for the active ingredients, and improves the spreadability and adhesiveness of the composition ingredients when applied to foliage as an aqueous pesticide formulation.

6 Claims, No Drawings

ENVIRONMENTALLY SAFE PESTICIDE COMPOSITIONS

This application is a division of application Ser. No. 07/907,050, filed Jul. 1, 1992; U.S. Pat. No. 5,342,630.

BACKGROUND OF THE INVENTION

Pesticide sales represent an important segment of the agrochemical industry in the United States and in other world markets, mainly for fungicide, herbicide and insecticide applications.

The control of phytopathogenic fungi is of great economic importance since fungal growth on plants or on parts of plants inhibits production of foliage, fruit or seed, and the overall quality of a cultivated crop.

Because of the vast economic ramifications of fungal propagation in agricultural and horticultural cultivations, a broad spectrum of fungicidal and fungistatic products have been developed for general and specific applications.

With respect to insecticide developments, a wide variety of ornamental and agricultural plants are susceptible to infestation by insects and arachnids. The pests inflict damage by consuming foliage and roots, withdrawing juices from the plants, secreting toxins, and infecting with diseases.

A broad scope of insecticide compounds have been developed to combat insects which are harmful to agricultural and horticultural plants. Illustrative of insecticide compositions are those described in U.S. Pat. Nos. 3,217,037; 3,506,698; 3,576,834; 3,636,111; 3,755,364; 3,875,232; 4,028,413; 4,128,581; 4,415,743; 4,640,927; 4,804,653; 4,839,349; 5,010,068; 5,087,456; 5,087,456; 5,096,928; and references cited therein.

The application of pesticides has contributed significant increases in ornamental and agricultural plant productivity. However, it has become increasingly apparent that the widespread use of synthetic organic pesticides has caused detrimental environmental effects which are harmful to mammals and other animals. Regulatory guidelines have encouraged a search for potentially less dangerous pesticidal chemicals.

Of particular interest with respect to the present invention are agrochemical compositions which include an environmentally safe pesticidal ingredient such as a fatty acid salt. SAFER Insecticidal Soap is an available commercial product which includes an alkali metal fatty acid salt as an active pesticidal ingredient. This type of pesticidal soap product in the form of an aqueous formulation is described in publications such as U.S. Pat. No. 5,093,124.

There remains a continuing need for the development of new and more effective agrochemical compositions which possess preventive, curative and systemic biological activity for the protection of cultivated plants, with a minimum of ecologically harmful side effects.

Accordingly, it is an object of this invention to provide an agrochemical composition which is a novel combination of inorganic and organic compounds exhibiting pesticidal properties.

It is another object of this invention to provide a particulate dry blend composition or aqueous formulation which is a combination of ingredients which include a bicarbonate-containing inorganic ingredient which exhibits fungicidal activity, and which enhances the biocidal activity of an environmentally safe insecticide ingredient.

Other objects and advantages of the present invention shall become apparent from the accompanying description and examples.

DESCRIPTION OF THE INVENTION

One or more objects of the present invention are accomplished by the provision of a pesticide composition which is a dry blend formulation comprising (1) an inorganic salt ingredient selected from alkali metal and ammonium bicarbonates, and (2) an ingredient selected from $C_8$–$C_{22}$ fatty acids and alkali metal and ammonium salts thereof; wherein the composition exhibits fungicidal and insecticidal activities.

The inorganic salt ingredient is selected from compounds which include sodium bicarbonate, potassium bicarbonate, lithium bicarbonate and ammonium bicarbonate. In a further embodiment, the inorganic salt ingredient can include an additional compound selected from sodium carbonate, potassium carbonate, lithium carbonate and ammonium carbonate.

Illustrative of inorganic salt ingredients in a formulation are sodium, potassium, lithium or ammonium bicarbonate; or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; sodium bicarbonate and potassium carbonate; potassium bicarbonate and potassium carbonate; and the like.

Multiple inorganic salt compounds can be utilized in a broad range of molar quantities relative to each other. The molar quantity of a carbonate salt compound normally is determined by pH control considerations when aqueous formulations are prepared. The content of a carbonate salt compound can be varied to control the pH at a desired level in the range of 7.5–12. Aqueous pesticidal formulations of the present invention tend to have a higher biocidal activity at higher pH values.

The average particle size diameter of the inorganic salt ingredient typically will be in the range between about 10–600 microns. Improved formulation properties are obtained when the inorganic salt particles have an average particle size diameter in the range between about 0.1–1 micron, and lower.

The $C_8$–$C_{22}$ fatty acid ingredient and alkali metal and ammonium salts thereof are selected from natural straight chain and synthetic branched chain fatty acids, which have a saturated or unsaturated structure.

Illustrative of natural fatty acids are caprilic acid, pelargonic acid, capric acid, lauric acid, myristic acid, palmitic acid, stearic acid, oleic acid, linoleic acid, arachidic acid, behenic acid, cetoleic acid, and the like.

The $C_8$–$C_{22}$ fatty acid ingredient can consist of two or more saturated or unsaturated carboxylic acids such as those derived from beef and mutton tallow, lard, cottonseed oil, palm oil, and the like.

Palm fatty acid distillate is a commercial product produced by distilling the fatty acids present in natural palm oil. A distillate product typically has the following weight percent content:

| | |
|---|---|
| Free fatty acids | 60–90 |
| Water | <1 |
| Triglycerides | 10–40 |
| Unsaponifiables | <3 |

The iodine value is less than 54 and the melting point is about 45° C. The content of peroxides is below 10 milliequivalents of oxygen per kilogram. The fatty acids in the free fatty acids and the triglycerides consist of the following weight percent:

| Palmitic acid | 38–50 |
|---|---|
| Oleic acid | 35–40 |
| Linoleic acid | 5–10 |
| Stearic acid | 3–6 |
| Lauric acid | 1–3 |

Beef tallow acids are available commercially as a byproduct obtained by alkaline extraction of waste beef fat and subsequent acidification, and normally contain the following weight percent of fatty constituents:

| Free fatty acids | 60–90 |
|---|---|
| Triglycerides | 10–40 |
| Water | <1 |
| Unsaponifiables | <3 |

The iodine value is less than 50 and the melting point is 40°–45° C. The content of peroxides is less than 10 milliequivalents of oxygen per kilogram. The fatty acids in the free fatty acids and in the triglycerides have the following weight percent content:

| Palmitic acid | 22–28 |
|---|---|
| Oleic acid | 38–44 |
| Linoleic acid | 3–6 |
| Stearic acid | 18–24 |

Because $C_8$–$C_{22}$ fatty acids and glycerides are susceptible to atmospheric oxidation, it is advantageous to incorporate an oil-soluble antioxidant, and a chelating agent to bind any ferric, copper, zinc or other metal capable of catalyzing atmospheric oxidation. Suitable quantities for inclusion in the fatty acid bulk are about 0.03–0.1% or higher of antioxidant as permitted by regulation, and about 0.05–0.3% of chelating agent, based on the weight of fatty acid.

Illustrative of preferred additives are butylated hydroxytoluene antioxidant, and citric acid and ethylenediamine tetraacetate chelating agents. The chelating agent is added in a solvent such as propylene glycol to facilitate blending into the fatty acid.

A $C_8$–$C_{22}$ fatty acid salt of an invention composition is prepared by reacting the free fatty acid component with an appropriate basic alkali metal or ammonium compound, such as a carbonate, bicarbonate or hydroxide derivative.

A $C_8$–$C_{22}$ fatty acid salt ingredient can be added to an invention composition as a previously prepared compound, or the salt can be formed in situ by the incorporation and blending of $C_8$–$C_{22}$ fatty acid and basic alkali metal or ammonium bicarbonate ingredients.

The content of fatty acid ingredient in an invention composition normally will vary in the range between about 40–90 weight percent.

The content of inorganic salt ingredient in an invention composition typically is between about 0.05–1.5 parts by weight per part of $C_8$–$C_{22}$ fatty acid ingredient.

If an invention dry blend pesticide formulation is to be utilized as a dusting powder, the content of $C_8$–$C_{22}$ fatty acid ingredient can vary in the range between about 0.1–5 weight percent, and the main bulk of the formulation is a particulate inert diluent. Illustrative of inert diluents are bentonite, calcium carbonate, magnesia, gypsum, kieselguhr, diatomaceous earth, and the like. Granules or larger particles can be formed by pelleting an invention pulverulent pesticide composition in admixture with a powdered inert diluent.

An invention pesticide composition also can be formulated as a concentrate, which subsequently is diluted before application to plant life. The content of $C_8$–$C_{22}$ fatty acid ingredient in a concentrate can vary in the range between about 5–30 weight percent and higher, before blending with an inert diluent.

In another embodiment this invention provides an aqueous pesticide formulation having an ingredient content which comprises (1) an inorganic salt ingredient selected from alkali metal and ammonium bicarbonates; and (2) a salt ingredient selected from $C_8$–$C_{22}$ fatty acid alkali metal and ammonium salts; wherein the formulation exhibits fungicidal and insecticidal activities.

The types and proportions of ingredients in an invention aqueous pesticide formulation generally correspond to those employed in the invention dry blend compositions.

The content of $C_8$–$C_{22}$ fatty acid salt ingredient typically is between about 0.1–30 weight percent, based on the aqueous formulation weight. The content of inorganic salt ingredient is between about 0.05–1.5 parts by weight per part of $C_8$–$C_{22}$ fatty acid salt ingredient.

An invention aqueous pesticide formulation can be prepared in diluted form for direct usage, with a $C_8$–$C_{22}$ fatty salt content between about 0.1–5 weight percent. If the aqueous formulation is prepared as a concentrate, the $C_8$–$C_{22}$ fatty acid salt content can be between about 5–30 weight percent and higher, before dilution with water.

An invention dry blend pesticide composition or aqueous pesticide formulation optionally can contain a compatibility enhancing ingredient, such as a water-soluble organic compound which is in solid form at a temperature below about 10° C., and has a low vapor pressure at ambient temperatures. The content of compatibility enhancing ingredient can vary between about 0.5–20 weight percent, based on the weight of $C_8$–$C_{22}$ fatty acid and inorganic salt ingredients.

Water-soluble organic compounds having a low vapor pressure which can function as a compatibility enhancing ingredient include acetamide, acetylurea, alanine, aminoquanidine, aminopyridine, arabinose, benzenesulfonate salt, benzoate salt, citrate salt, cyclohexanol, dihydroxyacetone, dihydroxyacetone phosphate salt, dimethylurea, ethanolamine, ethylurea, ethylenedisulfonate salt, paraformaldehyde, fucose, glycerol, glycerol nitrate, glycerol phosphate salt, glycogen, glycolic aldehyde, glyoxal, hexamine, mannitol, fructose, glucose, hydroxyurea, lactose, maltose, maltodextrin, methyl glucoside, methylhydantoin, methylinositol, methylthiourea, methyluracil, methylurea, nitropentanediol, nitrourethane, pentaglycerol, phenylenediamine, polydextrose, ribose, semicarbazide, succinimide, sucrose, tetrahydroquinoline, tetrazine, thiourea, threonine, triaminobenzene, triazole, triethylphosphine oxide, triethylenetetramine, trihydroxybenzene, trimethylurea, trioxane, urea, xylose, xylylene glycol, polyvinylpyrrolidone, sodium carboxymethylcellulose, polyoxyalkylene glycol, polyalkylene oxide, xanthan gum, guar gum, locust bean gum, gum acacia, gum tragacanth, alginate salt, potato agar, and the like. A water-soluble polyhydroxy or polyoxyalkylene organic compound is a preferred type of compatibility enhancing ingredient.

The term "water-soluble" as employed herein refers to an organic compound which has a solubility of at least about one gram per 100 grams of water at 25° C.

The ingredients in an invention pesticide composition can be selected to include nitrogen, phosphorus and potassium elements, in a ratio that allows the composition to function as a fertilizer in addition to its function as a pesticide, when applied to agricultural and horticultural plants.

An agrochemical fertilizer ingredient can be selected from nitrogen-containing and phosphorus-containing compounds such as urea, melamine, hexamine, benzoquanamine, dicyanodiamide, ammeline, cyanuric acid, melamine nitrate, triethyl phosphite, calcium hydrogen phosphate, ammonium phosphate, potassium nitrate, and the like.

In a further embodiment this invention provides a pet shampoo formulation which is an aqueous medium having an ingredient content which comprises (1) a salt ingredient selected from $C_8$–$C_{22}$ fatty acid alkali metal and ammonium salts; (2) an inorganic salt ingredient selected from alkali metal and ammonium bicarbonates; and (3) a fragrance ingredient.

The content of $C_8$–$C_{22}$ fatty acid salt ingredient can vary between about 5–20 weight percent, based on the formulation weight.

The content of inorganic salt ingredient is between about 0.05–0.8 part by weight per part of $C_8$–$C_{22}$ fatty acid ingredient.

Volatile organic compounds suitable as the fragrance ingredient include amyl salicylate, citronellol, citronelloxyacetaldehyde, cyclamen aldehyde, citronellyl isobutyrate, coumarin, cyclohexyl acetate, cyclohexyl butyrate, diethyl malonate, ethyl 2-acetyl-5-ketohexanoate, isobornyl acetate, linalool, phenethyl alcohol, undecanol, alpha-hexylcinnamaldehyde, 2-methylhexanol, hexalon, phenylacetaldehyde, cis-3-hexen-1-ol, cyclamal, veronol, eugenol, Lyral, Galaxolide, Citralva, musk ambrette, terpinyl acetate, geraniol, alpha-damascone, alpha-methylionone, and the like.

Illustrative of volatile essential oils are oil of Bergamot, cedar leaf, cedar wood, geranium, lavender, white cedar, sandalwood oil, rose extract, violet extract, galbanum oil, and the like.

Synthetic types of organic fragrances are described in publications such as U.S. Pat. Nos. 4,314,915; 4,411,829; and 4,434,306.

A pet shampoo formulation of the present invention can contain other ingredients which improve the formulation properties, such as foam builders, foam stabilizers, preservatives, pH stabilizers, and the like. A preferred pet shampoo formulation contains between about 0.2–7 weight percent of a foam building ingredient, as illustrated by free $C_8$–$C_{22}$ free fatty acids, and $C_8$–$C_{22}$ fatty acid amides such as cocamide MEA (monoethanolamide), cocamide DEA (diethanolamide), lauramide DEA, lauric isopropylamide, stearamide MEA, palmitic amide MEA, oleic amide MEA, and the like.

A pet shampoo of the present invention can be used with safety for controlling fleas, and for cleaning and deodorizing pets on a regular schedule.

A pesticide composition of the present invention has a novel combination of properties for the practice of fungus and insect control in agricultural and horticultural applications.

An important feature of an invention dry blend pesticide composition or aqueous pesticide formulation is the exclusive use of ingredients which are environmentally safe. None of the invention active ingredients are harmful to mammals or other animals under application conditions.

A compound of the inorganic salt ingredient exhibits fungicidal properties, and the efficacy of the $C_8$–$C_{22}$ fatty acid insecticide ingredient is enhanced by the presence of the inorganic salt ingredient. A lesser quantity of insecticide ingredient then can be employed to achieve a desired degree of pest control.

A preferred feature of a present invention pesticide composition is the inclusion of a compatibility enhancing agent as an optional ingredient. Migration and settling of solid ingredients is minimized, and a dry blend composition has a more uniformly distributed content because of the presence of the compatibility enhancing ingredient. An aqueous pesticide formulation has exceptional long term stability, without phase separation and precipitation of solids when a compatibility enhancing ingredient is present.

As a further advantage, a present invention aqueous pesticide formulation has improved spreadability and adhesiveness when applied to plant foliage, and resists post-application pesticide drift. An applied formulation also exhibits humectant properties on coated foliage, and increased insecticidal efficacy because of the synergistic combination of inorganic and organic ingredients. The basic pH provided by the inorganic salt ingredient increases the potency of the $C_8$–$C_{22}$ fatty acid insecticide ingredient, and the rate of insect extermination is accelerated.

The following examples are further illustrative of the present invention. The components and specific ingredients are presented as being typical, and various modifications can be derived in view of the foregoing disclosure within the scope of the invention.

EXAMPLE I

This Example illustrates the preparation of a fungicide-insecticide dusting powder in accordance with the present invention.

The following ingredients are provided in the indicated proportions:

|  | Parts |
|---|---|
| $NaHCO_3$ | 10 |
| $K_2CO_3$ | 5 |
| pelargonic acid | 2 |
| capric acid | 2 |
| talc | 80 |

The active ingredients are blended with the talc and milled to a dry pulverulent composition having a particle size less than 0.5 micron.

The dusting powder is effective for keeping agricultural and horticultural plants free of fungi and insects.

EXAMPLE II

This Example illustrates the preparation of fungicide-insecticide composition tablets which rapidly disintegrate and disperse in water.

|  | Parts |
|---|---|
| palm fatty acid distillate sodium salt[2] | 20 |
| $NaHCO_3$ | 25 |
| citric acid | 10 |
| Lomar PWA 10[1] | 10 |
| polyethylene glycol (M.W. 4000) | 10 |
| sodium lignosulfonate | 2 |

[1] sodium salt of alkylarylsulfonate condensation product (Jacques Wolf & Co.)
[2] Lauric acid 2.3%
Palmitic acid 49.9%
Stearic acid 5.4%
Oleic acid 35.0%
Linoleic acid 7.4%

The active ingredients are blended with the citric acid, Lomar PWA, polyethylene glycol and sodium lignosulfonate ingredients, and the blend is formed into tablets which disintegrate and disperse in water within about six minutes at 25° C.

EXAMPLE III

This Example illustrates the preparation of a fungicide-insecticide emulsion formulation in accordance with the present invention.

|  | Parts |
| --- | --- |
| potassium oleate | 10 |
| potassium stearate | 10 |
| potassium palmitate | 10 |
| KHCO$_3$ | 10 |
| K$_2$CO$_3$ | 10 |
| sorbitol | 10 |
| ethoxylated sorbitan monolaurate | 2 |
| water | 50 |

The solid ingredients are blended, and the blend is suspended in water to form an aqueous emulsion.

The emulsion formulation is diluted with water to 3% by weight fatty acid salt ingredient. The diluted formulation is tested as a pesticidal medium against plant foliage infested with aphids, mites or small caterpillars, respectively. The pesticidal medium is 100% effective with each type of insect.

EXAMPLE IV

This Example illustrates the preparation of an acaricide-fertilizer composition for application to plant soil.

|  | Parts |
| --- | --- |
| melamine | 30 |
| urea | 30 |
| potassium glycerol phosphate | 20 |
| oleic acid | 5 |
| stearic acid | 5 |
| KHCO$_3$ | 15 |

The active ingredients are blended with the melamine, urea and potassium glycerol phosphate ingredients. Granules are prepared by tumbling the blend, spraying added water to form tacky solids, and then drying the granulated product.

EXAMPLE V

This Example illustrates the preparation of a pet shampoo.

|  | Parts |
| --- | --- |
| potassium oleate | 10 |
| potassium palmitate | 5 |
| propylene glycol | 8 |
| ethylene glycol monostearate | 1 |
| KHCO$_3$ | 5 |
| K$_2$CO$_3$ | 2 |
| Rhodamine B | 0.0001 |
| Lemongrass oil | 0.1 |
| cocamide MEA | 2 |

A shampoo is prepared by blending the listed ingredients with 75 parts of water.

What is claimed is:

1. A pet shampoo formulation which is an aqueous medium having an ingredient content which comprises (1) a salt ingredient selected from $C_8$–$C_{22}$ fatty acid alkali metal and ammonium salts; (2) an inorganic salt ingredient selected from alkali metal and ammonium bicarbonates; (3) a fragrance ingredient; and (4) at least one compound selected from alkali metal and ammonium carbonates providing a pH in the range of 7.5–12.

2. A shampoo formulation in accordance with claim 1 wherein the content of $C_8$–$C_{22}$ fatty acid salt ingredient is about 5–20 weight percent, based on the formulation weight.

3. A shampoo formulation in accordance with claim 1 wherein the content of inorganic salt ingredient is between about 0.05–0.8 part by weight per part of $C_8$–$C_{22}$ fatty acid salt ingredient.

4. A shampoo formulation in accordance with claim 1 wherein the content of $C_8$–$C_{22}$ fatty acid salt ingredient is selected from pelargonic acid, capric acid, lauric acid, palmitic acid, stearic acid, oleic acid and linoleic acid alkali metal and ammonium salts.

5. A shampoo formulation in accordance with claim 1 which additionally contains a foam building ingredient.

6. A pet shampoo in accordance with claim 1 which contains a $C_8$–$C_{22}$ fatty acid amide foam building ingredient.

* * * * *